United States Patent [19]

Carpenter et al.

[11] Patent Number: 4,483,922

[45] Date of Patent: Nov. 20, 1984

[54] INACTIVATION OF ENZYMES

[75] Inventors: Charles R. Carpenter, Seguin; Robert H. Dodge, New Braunfels; Kenneth A. Rosanoff, Seguin, all of Tex.

[73] Assignee: AMF Inc., White Plains, N.Y.

[21] Appl. No.: 378,441

[22] Filed: May 14, 1982

[51] Int. Cl.³ .................. C12N 9/99; C12Q 1/00; C12Q 1/44; C12Q 1/42; C12Q 1/32
[52] U.S. Cl. .................. 435/184; 435/4; 435/19; 435/21; 435/26
[58] Field of Search .............. 435/184, 4, 19, 26, 435/21

[56] References Cited

U.S. PATENT DOCUMENTS 4,279,994 7/1981 Huang .................. 435/19
4,311,791 1/1982 Bernstein .............. 435/26

OTHER PUBLICATIONS

Schweizer et al., Chemcial Abstracts 78: 39986m, (1973).

*Primary Examiner*—Lionel M. Shapiro
*Attorney, Agent, or Firm*—David E. Dougherty; Michael E. Zall

[57] ABSTRACT

A method for inactivating enzymes, particularly enzymes found in human serum. The method comprises reacting the enzyme in a suitable medium, e.g. human serum, with an inactivating amount of peracetic acid. In the preferred embodiment the treated serum is subsequently neutralized and dialyzed. Preferably, the serums are used as standards for calibration or as a control in assay kits, e.g. RIA, and EIA or enzyme kits, for the determination of specific ligands and enzymes.

15 Claims, No Drawings

INACTIVATION OF ENZYMES

BACKGROUND OF THE INVENTION

1. Field of the Invention

This invention relates to the inactivation of enzymes, more particularly to a method of reducing enzyme activity in blood serum, e.g. human blood serum.

2. Prior Art

Blood serum is a complex biological fluid containing numerous components of substantial physiological importance. In a normal healthy person, the concentrations of these components fall within certain reasonably well defined limits. When one or more of these components is determined upon analysis to fall outside of these acceptable limits, various diseases or pathological conditions of the body system are indicated. The rapid analysis of various blood serum components has thus became a valuable adjunct in the clinical diagnosis of disease. In recent years, novel automated and non-automated procedures and assay kits have been developed for the rapid analysis of the multiple components of blood serum. These procedures and kits are capable of determining the concentrations of a host of blood serum enzyme levels in a blood sample, for example, alkaline phosphatase, lactate dehydrogenase (LDH), transaminases (SGOT), and (SGPT), (GGT), and creatinine phosphokinase (CPK). Immunoassay procedures are available for determining the serum levels of components such as gastrin and insulin.

In the performance of such analytical tests on blood serum and other biological samples, it is necessary to use laboratory serum standards for purposes of calibration and control testing. Accurate results in the use of these test procedures and kits are dependent upon such serum standards.

Such standards for calibration and control are often difficult, if not impossible to obtain by known procedures. For example, in the determination of certain specific enzymes, e.g. alkaline phosphatase, GGT, LDH, lipase, SGOT, it is difficult and expensive to obtain stable standard serums, particularly human serum having a controlled or reduced, e.g. zero, level of such enzymes. For example, lipase free injectable human serum albumin must often be used as a substitute for lipase free human serum and bovine serum albumin is often used as a standard or base matrix for calibrators.

Enzyme deactivation is a known process and may be accomplished, for example, by heating the enzyme to a sufficient temperature to inactivate the enzyme. Such a method of inactivating enzymes is impractical when seeking to inactivate enzymes in serums, particularly human serums, for such heat treatment will generally destroy the usefulness of the serum and its components.

Alternatively, a number of chemical enzyme inactivators have been developed. Representative of such chemical inactivators are copper sulfate, barium peroxide, hydrogen peroxide, silver nitrate, mercuric chloride, sodium hypochloride, and cadmium chloride. Most of these inactivators have not been used to treat serums, however, if used, they would tend to be non-selective in that they would destroy the usefulness of the serum by destroying certain components thereof. Additionally, a number of these chemical inactivators are toxic, would discolor the serum and are relatively expensive to use.

More specifically, U.S. Pat. No. 2,647,854 to Pfannmuller et al describes the inactivation of enzymes with barium peroxide. The enzymes, e.g. amylases, are used to thin water suspensions of raw starch in preparing paper and textile sizes, starch coatings, laminating adhesives and the like. Acetic acid may be used to decrease the pH of the solution to thereby increase the solubility of the barium peroxide. Chemical inactivation with barium peroxide may also be utilized on other enzyme types.

U.S. Pat. No. 3,513,072 to Frankevicz et al is directed to the inactivation of alpha-amylase enzymes by fluorosilica compounds, to control starch liquefaction in a starch slurry.

U.S. Pat. No. 3,806,421 to Ueda et al describes an inhibitor for retarding or preventing decomposition of starch to glucose by amylase. The inhibitor is recovered from the culture broth of *Streptomyces flavochromogenes* 280.

U.S. Pat. No. 4,007,008 to Becker et al describes a method of treating animal serum to simulate human blood serum for use as a reference standard for automated biological testing instruments. Non-human serum, e.g. serum of bovine, equine, porcine, sheep, etc. are treated to decrease the enzyme activities in such serum to human levels, without alteration of other constituent levels normally found in human blood serum. Becker et al accomplishes such by elevation of the pH of the serum with a base, followed by neutralization with an acid to a normal pH. Of additional relevance is Example 2 in Becker et al which describes decolorizing natural serum by the controlled addition of small amounts of a mild oxidant.

U.S. Pat. No. 4,086,139 to Hoerle describes freeing the protease enzyme in a mixed protease-amylase enzyme composition of its amylase activity by treating the composition with "... an oxidizing agent selected from the group consisting of chlorite and hypo-chlorite ions ..." The ions are added to the mixture in an amount sufficient to inactivate the amylase to a greater degree than the protease. A preferred hypochlorite composition is CLOROX.

U.S. Pat. No. 4,184,848 to Batz et al describes the use of a specific group of polyethylene glycol esters for the elimination of turbidity in serum.

U.S. Pat. No. 4,264,471 to Briggs describes a process for obtaining delipified human serum or plasma of low turbidity. The process comprises simultaneously deionizing and pH adjusting the serum of plasma to near the isoelectric point of the lipoprotein.

Additionally, Sprossig et al, "Kaltsterilisation Von Seren Mit Peressigsaure", Journal of Hygiene, Epidemiology, Microbiology and Immunology, 20, 1976, No. 2 157–163 describes the use of low concentrations, i.e. 0.02% to 0.1%, of peracetic acid to sterilize serum used to prepare a culture medium for bacteria, mycoplasmas and tissue cultures.

Of additional interest are U.S. Pat. Nos. 3,986,930 to Kurooka et al and 4,279,994 to Huang which describe the determination of lipase enzyme in serum using chemical reagents containing sulphur. These patents also teach the use of enzyme inhibitors which specifically inactivate enzymes which interfere with the determination of lipase without inactivating lipase. These enzyme inhibitors are exemplified by phenylmethylsulfonyl fluoride (PMSF) and diisopropylfluorophosphate.

None of the aforementioned references, teach or suggest the invention described and claimed herein or the advantages in utilizing such invention, particularly in the treatment of human serum to produce a standard or control serum.

OBJECTS AND SUMMARY OF THE INVENTION

An object of this invention is to provide a convenient method of reducing the enzyme activity in a serum.

Another object of this invention is to provide a method of preparing human serum having reduced or substantially zero levels of enzyme activity without substantially affecting the other useful components of the serum.

Still another object of this invention is to provide a method for reducing various enzyme activities in a human serum to a substantially zero level.

A further object of this invention, is to provide a method for producing serum having reduced levels of enzymes and which is suitable for use as a serum standard or control in assay kits.

Still another object of this invention is to provide a serum standard or a control serum, particularly from human blood, which can be prepared in a simple and efficient manner at low cost with readily available materials and which is stable over long periods of time.

Still another object of this invention is to produce a human serum having reduced enzyme activity and which does not cause the degradation of certain enzyme sensitive labile peptides mixed therein thus permitting such serum-peptide mixtures to be utilized as standards in assay kits.

All of the foregoing objects, as well as others are achieved by the method of this invention for reducing enzyme activity in a serum. The method comprises contacting the serum with an enzyme inactivating amount of peracetic acid to produce a treated serum. Preferably, the serum is subsequently neutralized to a physiological normal pH and then dialyzed. The preferred serum for treatment is clarified human serum.

Enzymes which have been found to be inactivated by the method of this invention are alkaline phosphatase, gamma glutamyl transpeptidase (GGT), lactate dehydrogenase (LDH), lipase and creatinine phosphokinase (CPK). The method may, however, also be used to inactivate other enzymes in a suitable medium.

The preferred human serum is characterized by having a reduced enzyme activity and significantly reduced ability to degrade a labile peptide, e.g. gastrin, mixed therein. Such a serum is particularly useful as a standard for calibration or a control serum for diagnostic kits.

DETAILED DESCRIPTION OF THE INVENTION

This invention is primarily directed to the treatment of serum. By "serum" is meant the cell free liquid portion of blood remaining after clot formation and removal (factors involved in clotting are removed, i.e. fibrin). Generally, the serum is prepared by withdrawing whole blood from an animal, e.g. human, into a suitable container such as a test tube and kept undisturbed. Within a few minutes, clot formation occurs. The blood sample can then be centrifuged to compact the clots and squeeze out the fluid serum. Optionally, the blood sample is allowed to settle for several hours during which time the clots slowly contact and squeeze out the serum. The serum can then be separated from the clots by simple decantation.

The serum to be treated by this invention is preferably human serum, however, non-human serum, particularly the serum of animals such as bovine, equine, porcine, and sheep may also be treated.

Generally, frozen human serum is used for the process of this invention. Typically, the serum is allowed to thaw, preferably rapidly at 32° to 37° C. in a water bath. For safe handling in the laboratory, the serum should be non-pathogenic (HAA and VDRL negative).

Blood, be it animal or human, can be supplied from various sources and the original levels of various constituents will depend somewhat upon such factors as physiology, metabolic rate, diet, genetics, etc. As a result, it is the usual practice to assay a lot of serum to categorize the serum before processing in accordance with this invention.

The enzymes to be inactivated by the method of this invention are generally not limited to specific type enzymes. Serum proteins such as thyroxin binding globulin (TBG) may also be inactivated. The method is applicable to inactivating enzymes found both in serums, e.g. alkaline phosphatase, GGT, LDH, lipase, proteases, etc. and other sources such as those found in bacteria or yeast. The method of this invention, however, is particularly applicable to inactivating enzymes in serum.

The method comprises contacting the enzyme with an inactivating amount of peracetic acid. Any suitable liquid medium may be used which will permit the inactivation of the enzymes by the peracetic acid. An aqueous medium is the preferred medium with serum, particularly human serum, being the most useful application of this invention.

The inactivating amount of peracetic acid used will generally depend on the enzyme to be inactivated, the concentration of the enzyme, and the particular medium, e.g. human serum.

Generally, it has been found that there is a relatively sharp threshold concentration of peractic acid above which the inactivation of the enzymes is substantially complete. A range with human serum appears to be from about 0.1% to about 1% by volume, with a preferred range from about 0.2% to about 0.5% by volume.

Preferably, the peracetic acid is added to, for example serum, as a dilute solution in water, e.g. about 2% to 40%, and is added over a period of time of from about 15 to 180 minutes. Such a procedure is preferred in order to prevent degradation of the other constituents of the serum if too rapid or concentrated a solution is used.

The preferred method of this invention, comprises contacting the serum with an enzyme inactivating amount of peracetic acid followed by neutralization with a base to a physiological normal pH. By a physiological normal pH it is meant a serum with a pH of about 7.4 to 7.8. It is believed that such neutralization, besides rendering the serum useful for its preferred intended purpose, operates to terminate further oxidization of the enzymes.

Preferably, the serum is neutralized with a strong base such as KOH, NaOH, LiOH, quaternary ammonium compounds such as tetraethyl or tetramethyl ammonium hydroxide and the like. The preferred base is NaOH. It is preferred to use a concentrated solution of such base to minimize changes in volume.

Optionally, further reduction of the peroxides in the treated serum may be obtained by such agents, as butylated hydroxytoluene (BHT), citric acid or cystene to prevent additional oxidation.

In a preferred procedure, the serum is contacted with peracetic acid. When the desired levels of enzymatic activities are reached, as determined by a prior titration experiment, the process may be stopped by neutralization of the reaction system with the appropriate base to return the serum to the physiological normal pH.

It is preferred that after the treatment of the serum with peracetic acid and neutralization that the serum be dialyzed to aid in the removal of any of the by-products from such treatments. Such procedures are well known in the art.

The aforementioned process for treating serum is comparatively insensitive to temperature, however, it is desirable to maintain ambient temperature. It is thus preferred to carry out the treatments within the range of 20° to 30° C.

This procedure for inactivation of enzymatic activity in serum is selective in that it has a minimum effect on other constituents in the serum such as albumins and globulins, lipids, cholesterol, glucose and the like but is specific for enzymes.

Although this invention has as its primary use, treating human blood serum, it may also have application to treating animal blood serum. A number of constituents in animal blood have been found to be present in concentrations which are not too different from the concentrations of the same constituents in human blood. However, differences do exist in some constituents, the more important of which are enzyme activities which are often elevated as much as 2 to 20 fold by comparison with human levels. Table 1 is a comparison of the enzyme activities in human blood with the enzyme activities in bovine, equine, and porcine sera.

TABLE I

| | ENZYME ACTIVITY IN INTERNATIONAL UNITS/LITER(IU/l) | | | |
|---|---|---|---|---|
| Enzymes | Human Serum | Bovine Serum | Equine Serum | Porcine Serum |
| ALK-Phos(1) | 6–110 | 24–70 | 115–216 | 60–100 |
| CPK(1) | 0–70 | 60–185 | 50–188 | 2000–2500 |
| LDH(2) | 20–63 | 350–900 | 344–780 | 653–700 |
| SGPT(2) | 3–17 | 20–45 | 15–22 | 48–60 |
| SGOT(2) | 4–13 | 61 | — | — |

(1)—30° C. Reaction
(2)—25° C. Reaction
*U.S. Pat. No. 4,007,008 (Col. 2).

Thus the method of this invention may be used to affect the reduction in the elevated enzyme activities in animal serum to within or below the normal human range level as well as reducing normal enzyme levels in human serum. This is accomplished both in human and animal serum without substantial alteration of the other constituent levels found in the blood serum or adversely affecting the desirable constituents of the serum.

The constituents of the serum processed in accordance with this invention may be adjusted in a number of ways.

When, for example, it is desired to raise the level of enzymatic activities to between the level of the original serum and that resulting from such treatment, the serum can be blended back with original serum to strike a desired level between their respective enzymatic activities, depending upon the amount of one blended with the other. Such blending allows for a minimal amount of added extrinisic enzyme.

Instead of blending as above, specific enzymes or other constituents, e.g. labile peptides, may be added to the processed serum to arrive at enzyme activities or analyte concentrations of constituents desired in the final product.

The blended serum as well as the serum produced in accordance with the practice of this invention can be lyophilized by conventional lyophilization procedures well known to those skilled in the art.

The method of this invention has many uses, in particular for preparing stable serum standards having reduced or substantially zero level enzymes. Such serum standards are used for calibration or as control serum in assay kits, both radio-immunoassay (RIA), enzyme-immunoassay (EIA) and enzyme kits. Generally these kits are used for the determination of specific blood components (ligands and enzymes), for example, lipase enzyme activity (see for example the aforementioned U.S. Pat. Nos. 3,986,930 to Kurooka et al and 4,279,994 to Huang) and gastrin and insulin concentrations. These latter kits require a stable control serum of these peptides in human serum.

The serum produced by the method of this invention is unique although perhaps difficult to biologically and chemically characterize. As shown in the Examples, when the enzyme levels, e.g., alkaline phosphatase, GGT, LDH, lipase and proteases are reduced, the serum does not degrade certain enzyme sensitive labile peptides mixed in the serum for at least 96 hours. This is indeed unexpected. This makes the serum of this invention particularly useful as a base matrix for certain labile peptides, insulin, gastrin, ACTH, etc., i.e. known added amounts of these peptides in the serum remain stable so that the serum-peptide mixture may be utilized as a standard serum.

Having described the basic concepts of this invention, illustration will now be made by way of specific examples applied to human serum, it being understood that the same treatment can be employed with the animal serum of the type described, by substitution of the serum of such other animals for the human serum in the following examples.

EXAMPLES

Preferred General Procedure for Treating Human Serum

1. Obtain 1000 ml of clarified human serum and thaw (if necessary) in 37° C. water bath. The protein concentration of the serum should be 7.0 g%±0.5 per liter.

2. Transfer the serum to a 2000 ml Erlenmeyer flask. Slowly mix the serum with the aid of a stir plate and magnetic stir bar.

3. Mix 9.0 ml of peracetic acid (40% by weight concentration) with 9 ml of distilled water and gently swirl to effect mixing.

4. Slowly add the acid solution to the serum as it mixes, with the aid of a peristaltic pump. The pump speed should be set so that it takes approximately one hour to complete the addition.

5. As the acid solution is added, the serum will become slightly clouded. Once all of the acid has been added, obtain a pH reading. The pH should be in the range of 4.4–4.9.

6. Neutralize the serum by adding 2N NaOH dropwise until the pH reaches 7.4. Allow the serum to stir for approximately 15 min. to insure that the pH is stabilized at 7.4.

7. Pour the serum into 75×50 mm Dialysis tubing with approximately 300 ml per sac and dialyze 2 days at 40° C. against several changes of phosphate buffer saline (PBS)(pH 7.4). 8. Remove the serum from the dialysis sacs and centrifuge at 14,000 RPM for 20 min. at 4° C.

minutes and then filtered through 0.45 um and 0.22 um Millipore filters.

TABLE II
ANALYSIS OF SERUM OF EXAMPLE 1

| COMPONENT | UNITS | REFERENCE VALUE** | BEFORE TREATMENT | AFTER TREATMENT |
|---|---|---|---|---|
| GLUCOSE | MG/DL | 70–110 | 2 | 1 |
| BUN | MG/DL | 10–26 | 2 | 2 |
| CREATININE | MG/DL | 0.6–1.5 | .2 | .2 |
| BUN/CREAT RATIO | — | 10–20 | 10 | 10. |
| URIC ACID | MG/DL | — | .6 | .4 |
| SODIUM | MEQ/L | 135–147 | 141 | 160+ |
| POTASSIUM | MEQ/L | 3.5–5.0 | 3.6 | 1.0 |
| CHLORIDE | MEQ/L | 100–110 | 104 | 130+ |
| CARBON DIOXIDE | MEQ/L | 24–34 | 27 | 0 |
| CALCIUM | MG/DL | 8.5–10.5 | 9.6 | 2.0 |
| ION-CA (APPROX) | MEQ/L | 1.9–2.3 | 2.1 | .4 |
| PHOSPHOROUS | MG/DL | — | .5 | 10+ |
| CHOLESTEROL | MG/DL | 140–270 | 3. | 6 |
| TRIGLYCERIDES | MG/DL | 10–200 | 0 | 0 |
| TOTAL PROTEIN | GM/DL | 6.0–8.0 | 6.9 | 5.6 |
| ALBUMIN | GM/DL | 3.5–5.0 | 4.6 | 3.5 |
| GLOBULINS | GM/DL | 2.3–3.5 | 2.3 | 2.1 |
| A/G RATIO | — | 1/.0–2.2 | 2.0 | 1.7 |
| TOTAL BILIRUBIN | MG/DL | — | .1 | .2 |
| *ALK PHOS | MU/ML | — | 85 | 5 |
| *GGT | MU/ML | — | 10 | 0 |
| *SGOT | MU/ML | 0.40 | 20 | 20 |
| *LDH | MU/ML | 100–225 | 19 | 0 |
| IRON | MCG/DL | 60–150 | 104 | 70 |

**Human blood
*Enzymes
CPK is also inactivated in a Beckman J-2 centrifuge.

9. Combine the supernatants in a suitable glass container and obtain a pH reading (readjust to 7.4 if necessary).

10. Obtain a serum protein level by means of refractometer. Adjust the protein level to within the range of 4.5–5.0 g% protein per liter.

11. Assemble a Millipore 142 mm filter housing with a 0.45 um filter.

12. Filter the serum through the 0.45 um membrane filter (changes of filter may be necessary upon clogging).

13. Reassemble the 142 mm filter housing with a 0.22 um filter.

14. Filter the serum through the 0.22 um membrane filter at least three times.

15. Sterile filter the serum through a 0.22 um filter into pre-sterilized 500 mL bottles then store frozen for future use.

EXAMPLE I

One thousand ml of clarified human serum was thawed and put into a 2 l Erlenmeyer flask.

9 ml of peracetic acid (40% concentration) was mixed with 91 ml of deionized water to produce a 9.0% peracetic acid solution.

This was added to the serum while stirring over a period of 2 hours. A peristaltic pump was used.

The final peracetic acid concentration of the serum was 0.818%. The pH of the serum after the addition of peracetic acid was 4.5. The serum was neutralized immediately after acid treatment by adding 2N NaOH until the pH reached 7.4. The peracetic acid was removed from the serum by dialyzing the serum through several volume changes of PBS at pH 7.4. The final serum produced was then centrifuged at 14,000 RPM for 15

EXAMPLE II
Preparation of Gastrin Standard Serum 50 ug of synthetic gastrin (obtained from Calbiochem) was dissolved in 100 ml of the treated serum of Example I. This provided a 0.5 ug/ml gastrin solution.

Further dilutions from this stock were made using the serum of Example I.

50 ng/ml–1 ml of 0.5 ug/ml stock Q.S. to 10 ml.
5 ng/ml–100 ul of 0.5 ug/ml stock Q.S. to 10 Ml
500 pg/ml–10 ul of 0.5 ug/ml stock Q.S. to 10 ml
50 pg/ml–1 ml of the 500 pg/ml dilution Q.S. to 10 ml 0.1% sodium azide was added to these standards and they were stored at 4° C. The 500 pg/ml and 50 pg/ml standards, along with the treated neat serum of Example I, were run in a commercially available Gastrin Assay.

A 500 pg/ml standard was prepared in a similar manner in normal clarified human serum.

Stability studies were run on these standards stored at 4° C. by running them in the gastrin assay twice a week for about 2 months. The results generated from these assays are as follows:

TABLE III
STABILITY

| Days | 50 pg/ml Std Assayed Value (pg/ml) | 500 pg/ml Std Assayed Value (pg/ml) | 500 pg/ml Std in normal human serum Assoyed Value |
|---|---|---|---|
| 0 | 38 | 518 | 475 |
| 3 | 39 | 600 | — |
| 6 | 64 | 609 | 100 |
| 12 | 70 | 545 | 80 |
| 21 | 74 | 552 | 18 |
| 26 | 86 | 656 | — |
| 30 | 67 | 555 | — |
| 32 | 63 | 608 | — |
| 36 | 63 | 605 | — |

TABLE III-continued

| | STABILITY | | |
|---|---|---|---|
| Days | 50 pg/ml Std Assayed Value (pg/ml) | 500 pg/ml Std Assayed Value (pg/ml) | 500 pg/ml Std in normal human serum Assoyed Value |
| 38 | 63 | 610 | — |
| 45 | 80 | 543 | — |
| 51 | 79 | 581 | — |

The foregoing indicates that gastrin in the presence of the serum of this invention is stable over a long period of time. The increasing levels of gastrin over time indicate that the gastrin standard used in the assay was deteriorating.

Gastrin in the presence of normal untreated serum degrades within 3 to 12 days.

Similar increases in stability were found with insulin in the presence of the serum of this invention.

EXAMPLE III

Four 100 ml aliquots of clarified human serum were treated with hydrogen peroxide. The concentrations of peroxide added were 0.33%, 1.7%, 5% and 10%. After addition of peroxide the samples foamed severely. There was 800 ml of foam in the beaker with 100 ml of serum during the treatment with 0.5% and 1.0% peroxide.

The samples containing peroxide were stirred at room temperature for a period of 1 hour and then dialyzed in 0.01M phosphate buffered saline for two hours at room temperature. The samples were removed from dialysis and filtered thru a 0.45 um Millipore filter. The filtered samples were analyzed. The results are shown in Table IV.

TABLE IV

| | 0.33%* | 1.7%* | 5%* | 10%* | Control* |
|---|---|---|---|---|---|
| Alkaline Phosphatase | 73 | 74 | 72 | 75 | 74 |
| GGT | 12 | 12 | 12 | 14 | 9 |
| SGOT | 9 | 9 | 16 | 86 | 30 |
| LDH | 189 | 196 | 173 | 146 | 182 |

*All result in MU/mL

What is claimed is:

1. A method of reducing enzyme activity in a serum with a minimum effect on other constituents in the serum comprising contacting the serum with an enzyme inactivating amount of a peracetic acid to produce a treated serum, wherein the inactivating amount is from about 0.2% to about 1% peracetic acid by weight of serum, wherein said serum does not degrade an amount of enzyme sensitive labile peptide mixed therein for at least about 96 hours, and wherein the enzymes are selected from the group consisting of:
 alkaline phosphatase,
 proteases,
 gamma glutamyl transpeptidase (GGT),
 lactate dehydrogenase (LDH),
 creatinin phosphokinase (CPK), and
 lipase.

2. The method of claim 1, further comprising neutralizing the treated serum to a physiological normal pH to produce a neutralized serum.

3. The method of claim 2, further comprising dialyzing the neutralized serum.

4. The method of claim 1, wherein the serum is human serum.

5. The method of claim 1, wherein the serum is clarified human serum.

6. The method of claim 4, wherein the inactivating amount is from about 0.2% to about 0.5% peracetic acid by weight of serum.

7. The method of claim 2, wherein the treated serum is neutralized with sodium hydroxide to a pH of about 7.4 to 7.8.

8. The method of claim 2, wherein the treated serum is neutralized with sodium hydroxide to a pH of about 7.4.

9. The method of claim 1, wherein the enzyme is alkaline phosphatase.

10. The method of claim 1, wherein the enzyme is gamma glutamyl transpeptidase (GGT).

11. The method of claim 1, wherein the enzyme is lactate dehydrogenase (LDH).

12. The method of claim 1, wherein the enzyme is lipase.

13. The method of claim 1, wherein the labile peptide is gastrin.

14. The method of claim 1, wherein the labile peptide is insulin.

15. The method of claim 1, wherein the labile peptide is adenocorticotrophic hormone (ACTH).

* * * * *